United States Patent [19]

Anderson et al.

[11] 4,189,598

[45] Feb. 19, 1980

[54] PHENOXYBENZYL 2-[2-(2-HYDROXY)INDANYL]-3-METHYL-BUTANOATES

[75] Inventors: Richard J. Anderson; Clive A. Henrick, both of Palo Alto, Calif.

[73] Assignee: Zoecon Corporation, Palo Alto, Calif.

[21] Appl. No.: 927,315

[22] Filed: Jul. 24, 1978

[51] Int. Cl.$^2$ .................. C07C 69/76; C07C 121/75
[52] U.S. Cl. ........................ 560/56; 260/332.2 R; 260/347.4; 260/465 D; 424/304; 424/308; 560/8; 562/405
[58] Field of Search ............... 560/56; 260/465 D

[56] References Cited

U.S. PATENT DOCUMENTS

| | | | |
|---|---|---|---|
| 3,312,730 | 4/1967 | Winter et al. | 560/56 |
| 3,910,954 | 10/1975 | Jirkovsky et al. | 260/327 TH |
| 3,966,959 | 6/1976 | Addor | 424/304 |
| 4,016,179 | 4/1977 | Fujimoto et al. | 560/56 |

OTHER PUBLICATIONS

Ahmed et al., Chemical Abstracts, vol. 55, 3531–3532 (1960).

*Primary Examiner*—Dolph H. Torrence
*Attorney, Agent, or Firm*—Donald W. Erickson

[57] ABSTRACT

Esters of α-indenyl substituted aliphatic acids, intermediates therefor, synthesis thereof, and the use of said esters and compositions thereof for the control of pests.

11 Claims, No Drawings

PHENOXYBENZYL 2-[2-(2-HYDROXY)INDANYL]-3-METHYL-BUTANOATES

This invention relates to novel esters of α-indenyl substituted aliphatic acids, novel intermediates therefor, synthesis thereof, and the control of pests.

The esters of the present invention are represented by the following formula (A):

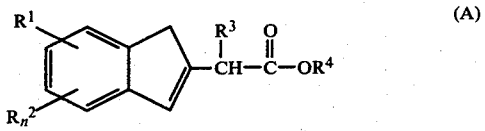
(A)

wherein, each of $R^1$ and $R^2$ is independently selected from hydrogen, chloro, fluoro, bromo, lower alkyl, lower alkoxy, and lower haloalkyl;

n is zero, one, two, or three;

$R^3$ is lower alkyl of 2 to 5 carbon atoms, lower alkenyl of 2 to 5 carbon atoms, or cyano; and $R^4$ is one of the groups

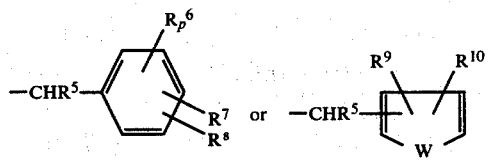

in which, p is zero, one, two, or three;

$R^5$ is hydrogen, cyano, methyl, or ethynyl;

$R^6$ is halogen, lower alkyl, lower haloalkyl, lower alkoxy, lower haloalkoxy, lower alkylthio, lower alkenyl, or lower haloalkenyl;

$R^7$ is hydrogen or together with $R^6$ forms a lower alkylenedioxy bridge across adjacent ring carbon atoms;

$R^8$ is hydrogen, lower alkenyloxy, lower alkynyl, lower alkynyloxy, lower haloalkynyl, lower alkylcarbonyl, arylcarbonyl, substituted arylcarbonyl, aryloxy, substituted aryloxy, arylthio, substituted arylthio, aralkyl, substituted aralkyl, cycloalkyl, cycloalkalkyl, lower acyloxy, aryloxycarbonyl, lower alkoxycarbonyl, or lower haloalkenyloxy;

W is oxygen or sulfur;

$R^9$ is hydrogen or lower alkyl; and $R^{10}$ is lower alkenyl, lower alkynyl, or aralkyl.

The compounds of the present invention represented by generic formula (A) are useful agents for the control of pests such as insects and acarids. Without any intention of being bound by theory and although the mode of action of the compounds of formula (A) as applied to the control of insects and acarids is not completely understood, the compounds of formula (A) appear to be effective for the control of insects and acarids by reason of mechanisms of the nature of the insect control agents known as pyrethrins and synthetic pyrethroids.

In the description hereinafter and the appended claims, each of $R^1$ through $R^{10}$, W, n and p is as defined hereinabove, unless otherwise specified.

The compounds of formula (A) can be synthesized by the reaction of 2-indanone or substituted 2-indanone of formula I with an α-halo ester of formula II to form a hydroxy ester III using a Reformatsky reaction. The hydroxy ester (III) is then dehydrated using, for example, p-toluenesulfonic acid, to form the indenyl ester (A). CF. Anderson, Jr. et al., J. Org. Chem. 38, 1439 (1973).

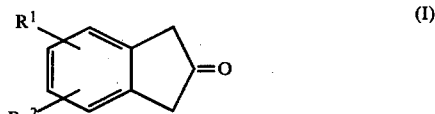
(I)

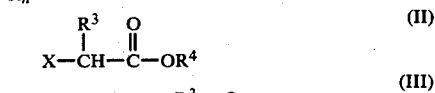
(II)

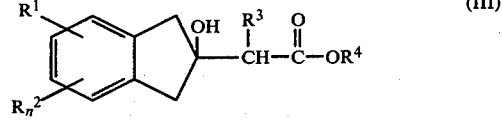
(III)

The compounds of formula I can be prepared from 1,2-bis(bromomethyl)benzenes using the method of Taylor et al., J. Med. Chem. 13, 1226 (1970).

The following terms, wherever used in the description herein and the appended claims, have the meaning defined below, unless otherwise specified hereinafter.

The term "lower alkyl" refers to an alkyl group, straight or branched, having a chain length of one to six carbon atoms. The term "lower haloalkyl" refers to an alkyl group substituted with one to three halogen atoms such as chloromethyl, fluoromethyl, trifluoromethyl, 2,2,2-trifluoroethyl, 6-chlorohexyl, 2-fluoroethyl, and the like. The term "lower alkoxy" refers to an alkoxy group, straight or branched, having a chain length of one to six carbon atoms. The term "lower alkylthio" refers to an alkylthio group, straight or branched, having a chain length of one to six carbon atoms.

The term "lower alkenyl" refers to an ethylenically unsaturated hydrocarbon group, straight or branched, having a chain length of two to six carbon atoms and one or two ethylenic bonds such as vinyl, allyl, 3-butenyl, 2-hexenyl, i-propenyl, 2,4-hexadienyl, and the like. The term "lower haloalkenyl" refers to a lower alkenyl group substituted with one to three halogen atoms. The term "lower alkenyloxy" refers to an alkenyloxy group, straight or branched, of three to six carbon atoms. The term "lower haloalkenyloxy" refers to a lower alkenyloxy group substituted with one to three halogen atoms.

The term "lower alkynyl" refers to an alkynyl group, straight or branched, having a chain length of two to six carbon atoms and one or two acetylenic bonds. The term "lower haloalkynyl" refers to a lower alkynyl group having one to three halogen atoms. The term "lower alkynyloxy" refers to an alkynyloxy group, straight or branched, of three to six carbon atoms.

The term "cycloalkyl" refers to a cycloalkyl group of three to six cyclic carbon atoms. The term "cycloalkalkyl" refers to a cycloalkyl group wherein one hydrogen atom is replaced by a lower alkyl group, the total number of carbon atoms being from four to eight, such as cyclopropanemethyl, cyclobutaneethyl, cyclohexanemethyl, and the like.

The term "aryl" refers to the aryl group phenyl or naphthyl. The term "aralkyl" refers to a lower alkyl group in which a hydrogen atom of the alkyl group is substituted by an aryl group, the total number of carbon atoms being from seven to twelve, such as benzyl, phenethyl, and the like. The terms "substituted aryl" and "substituted aralkyl" refer to an aryl group and an aralkyl group, respectively, substituted at one, two or three of the ring carbon atoms with a group selected from lower alkyl, lower haloalkyl, lower alkoxy, lower alkenyl, lower haloalkenyl, lower alkenyloxy, halogen, nitro, cyano, or alkylthio.

The term "lower haloalkoxy" refers to a lower alkoxy group substituted with one to three halogen atoms.

The term "lower acyloxy" refers to a lower aliphatic acyloxy group of one to six carbon atoms, such as acetoxy.

The compounds of the present invention of formula A have one or more asymmetric carbon atoms. The present invention includes each of the optical isomers and racemic mixtures thereof. In the examples hereinafter, unless otherwise specified, the compound prepared is a racemic mixture.

The compounds of the present invention of formula A are useful pest control agents, particularly for the control of insects and acarids. In the use of the compounds of Formula A for combatting insects and acarids for the protection of agricultural crops, for example soybeans, cotton, alfalfa, etc., a compound of formula A, or mixtures thereof, together with a carrier is applied to the locus in a pesticidally effective amount. The carrier can be liquid or solid and include adjuvants such as wetting agents, dispersing agents and other surface active agents. The compounds of formula A can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula A in the formulation can vary widely, generally within the range of about 0.01 percent to about 90.0 precent, by weight.

As shown hereinafter, the compounds of the present invention are effective on many different insects and on acarids. The compounds are effective control agents for insects such as mosquitoes, flies, aphids, weevils and acarids such as the spider mite and ticks. Depending upon the particular combination of the substituents of formula A herein, the compounds have a broad or relatively narrow spectrum of unusually high pesticidal activity on insects and acarids. Among the pests against which the compounds of the present invention are pesticidally effective are insects of the order Lepidoptera, Orthoptera, Heteroptera, Homoptera, Diptera, Coleoptera or Hymenoptera, and acarids of the order Acarina including mites of the family Tetranychidae or Tarsonemidae and ticks such as Ornithodoros.

The compounds of the present invention can be used in combination with other pesticides such as the carbamates, phosphates and insect growth regulators, e.g. propoxur, carbaryl, naled, dichlorvos, methoprene, kinoprene, hydroprene, cyhexatin, resmethrin, and permethrin.

The following examples are provided to illustrate the practice of the present invention. Temperature is given in degrees Centigrade. RT means room temperature.

EXAMPLE 1

A mixture of 1.95 g (30 mmol) purified zinc and 0.1 g mercuric chloride is stirred in 6 ml of benzene for 15 minutes. Then a solution of 1.32 g (10 mmol) 2-indanone and 4.3 g (12 mmol) m-phenoxybenzyl α-bromoisovalerate in 10 ml diethyl ether is added in portions over about 45 minutes. The reaction mixture is refluxed for about 4.5 hours. The reaction is then poured into ice cold 2 N sulfuric acid and extracted with chloroform. The organic phase is washed with sat. sodium bicarbonate and sat. sodium chloride solutions and dried over calcium sulfate. Solvent is removed under vacuum and pentane added to the residue, which is then filtered. The filtrate is applied to 4 (1m by 20 cm) preparative silica gel plates, which are then developed in 13% ethyl acetate/hexane. Removal of the band slightly more polar than starting 2-indanone gives m-phenoxybenzyl 2-[2-(2-hydroxy)indanyl]-3-methylbutanoate.

To a solution of 205 mg (0.49 mmol) of the above hydroxy ester in 5 ml benzene is added about 20 mg of p-toluene-sulfonic acid. The reaction mixture is heated at 80°, under nitrogen, for 24 hours. The reaction mixture is then poured into ether and 2 M sodium carbonate and the layers separated. The organic phase is washed with sat. NaCl solution, dried over calcium sulfate and solvent removed. The crude product is applied to a preparative silica gel plate and developed with 10% ethyl acetate/hexane and the major band removed to give m-phenoxybenzyl 2-(2-indenyl)-3-methylbutanoate, MS m/e 398 (M+).

EXAMPLE 2

A mixture of m-phenoxylbenzyl 2-(2-indenyl)-3-methylbutanoate (8 mmol), potassium hydroxide (24 mmol), ethanol (25 ml) and water (4 ml) is heated to reflux for about 3 hours. After cooling, the reaction is acidified with dilute hydrochloric acid. The mixture is extracted with ether, and the ether phase is washed to neutrality with saturated NaCl solution. Removal of solvent by evaporation yields 2-(2-indenyl)-3-methylbutanoic acid.

α-Cyano-m-phenoxybenzyl alcohol (8.5 g, 38 mmol) is dissolved in 150 ml ether and cooled in an ice-bath. To the solution is slowly added methanesulfonyl chloride (5.4 g, 47 mmol) in 20 ml ether. After the mixture is stirred about 20 minutes, triethylamine (4.76 g, 47 mmol) in 20 ml ether is added slowly and the mixture kept at 0° for 24 hours. Water is then added and the organic layer is separated, washed with 30% aqueous sodium bisulfite and water, dried and solvent removed under vacuum to yield α-cyano-m-phenoxybenzyl mesylate.

A mixture of 2-(2-indenyl)-3-methylbutanoic acid (3.4 mmol), potassium bicarbonate (3.4 mmol) in 10 ml of tetrahydrofuran/dimethylformamide (1/1) is stirred for a few minutes and then α-cyano-m-phenoxybenzyl mesylate (3.4 mmol) in 5 ml of tetrahydrofuran/dimethylformamide (1/1) is added. The reaction is worked up by diluting with ether, washing with water and sat. NaCl, drying and evaporating under vacuum to remove solvent to yield α-cyano-m-phenoxybenzyl 2-(2-indenyl)-3-methylbutanoate.

EXAMPLE 3

Following the procedure of Example 1, each of 5,6-dimethoxy-2-indanone, 5,6-dimethyl-2-indanone and 5-methyl-2-indanone is reacted with m-phenoxybenzyl α-bromoisovalerate to yield m-phenoxybenzyl 2-[2-(2-hydroxy-5,6-dimethoxy)indanyl]-3-methylbutanoate, m-phenoxybenzyl 2-[2-(2-hydroxy-5,6-dimethyl)indanyl]-3-methylbutanoate, and m-phenoxybenzyl 2-[2-(2-hydroxy-5-methyl)indanyl]-3-methylbutanoate.

Each of the 2-hydroxy esters is treated with p-toluenesulfonic acid as in Example 1 to yield m-phenoxybenzyl 2-(5,6-dimethoxy-2-indenyl)-3-methylbutanoate, m-phenoxybenzyl 2-(5,6-dimethyl-2-indenyl)-3-methylbutanoate, and m-phenoxybenzyl 2-(5-methyl-2-indenyl)-3-methylbutanoate.

Following the process of Example 2, each of the esters is hydrolyzed to the acid and then reacted with α-cyano-m-phenoxybenzyl mesylate to yield the respective α-cyano-m-phenoxybenzyl ester.

EXAMPLE 4

To 10 tetrahydrofuran (THF) is added 3,4,5,6-tetrafluoro-1,2-benzenedicarboxylic acid (2 g, 8.4 mmol). After cooling at 0°, 21.0 ml (20.9 mmol) of 1 M borane in THF is slowly added. The reaction mixture is allowed to rise to RT and stirred at RT for 18 hours and then is cooled and quenched with 10% HCl. The reaction mixture is added to ether, and the organic phase is washed with water, sat. sodium bicarbonate and brine, dried over sodium sulfate and evaporated under vacuum to yield 3,4,5,6-tetrafluoro-1,2-bis(hydroxymethyl)benzene.

To a solution of 3,4,5,6-tetrafluoro-1,2-bis(hydroxymethyl)benzene (1.5 g) in about 20 ml ether, in an ice bath, is slowly added phosphorus tribromide (1.3 g, 5 mmol) in about 10 ml ether. After about 2.5 hours, the reaction mixture is poured into ether (150 ml), and the organic phase is washed with water, dried over sodium sulfate and solvent evaporated to yield 3,4,5,6-tetrafluoro-1,2-bis(bromomethyl)benzene, which is then cyclized using the procedure of Taylor et al., supra, to yield 4,5,6,7-tetrafluoro-2-indanone.

EXAMPLE 5

Each of 5-chloro-2-indanone, 7-chloro-2-indanone, 5-trifluoromethyl-2-indanone, 5-bromo-2-indanone, 5-fluoro-2-indanone, 4-fluoro-2-indanone, 4,5-dichloro-2-indanone, 4,5,6,7-tetrachloro-2-indanone and 4,7-dibromo-5,6-dichloro-2-indanone is reacted with m-phenoxybenzyl α-bromoisovalerate using the procedure of Example 1 to yield the respective 2-hydroxyindanyl compound, under Column I.

I m-phenoxybenzyl 2-[2-(2-hydroxy-5-chloro)indanyl]-3-methylbutanoate
m-phenoxybenzyl 2-[2-(2-hydroxy-7-chloro)indanyl]-3-methylbutanoate
m-phenoxybenzyl 2-[2-(2-hydroxy-5-trifluoromethyl)indanyl]-3-methylbutanoate
m-phenoxybenzyl 2-[2-(2-hydroxy-5-bromo)indanyl]-3-methylbutanoate
m-phenoxybenzyl 2-[2-(2-hydroxy-5-fluoro)indanyl]-3-methylbutanoate
m-phenoxybenzyl 2-[2-(2-hydroxy-4-fluoro)indanyl]-3-methylbutanoate
m-phenoxybenzyl 2-[2-(2-hydroxy-4,5-dichloro)indanyl]-3-methylbutanoate
m-phenoxybenzyl 2-[2-(2-hydroxy-4,5,6,7-tetrachloro)indanyl]-3-methylbutanoate
m-phenoxybenzyl 2-[2-(2-hydroxy-4,7-dibromo-5,6-dichloro)indanyl]-3-methylbutanoate Each of the compounds under col. I is dehydrated using the procedure of Example 1 to yield the respective indenyl compound under col. II.

II m-phenoxybenzyl 2-(5-chloro-2-indenyl)-3-methylbutanoate
m-phenoxybenzyl 2-(7-chloro-2-indenyl)-3-methylbutanoate
m-phenoxybenzyl 2-(5-trifluoromethyl-2-indenyl)-3-methylbutanoate
m-phenoxybenzyl 2-(5-bromo-2-indenyl)-3-methylbutanoate
m-phenoxybenzyl 2-(5-fluoro-2-indenyl)-3-methylbutanoate
m-phenoxybenzyl 2-(4-fluoro-2-indenyl)-3-methylbutanoate
m-phenoxybenzyl 2-(4,5-dichloro-2-indenyl)-3-methylbutanoate
m-phenoxybenzyl 2-(4,5,6,7-tetrachloro-2-indenyl)-3-methylbutanoate
m-phenoxybenzyl 2-(4,7-dibromo-5,6-dichloro-2-indenyl)-3-methylbutanoate Each of the esters under col. II is hydrolyzed using the procedure of Example 2 to yield the respective acid under col. III.

III 2-(5-chloro-2-indenyl)-3methylbutanoic acid
2-(7-chloro-2-indenyl)-3-methylbutanoic acid
2-(5-trifluoromethyl-2-indenyl)-3-methylbutanoic acid
2-(5-bromo-2-indenyl)-3-methylbutanoic acid
2-(5-fluoro-2-indenyl)-3-methylbutanoic acid
2-(4-fluoro-2-indenyl)-3-methylbutanoic acid
2-(4,5-dichloro-2-indenyl)-3-methylbutanoic acid
2-(4,5,6,7-tetrachloro-2-indenyl)-3-methylbutanoic acid
2-(4,7-dibromo-5,6-dichloro-2-indenyl)-3-methylbutanoic acid The α-cyano-m-phenoxybenzyl esters of the acids under col. III of the present invention can be prepared by reaction with α-cyano-m-phenoxybenzyl mesylate by the process of Example 2.

The foregoing 2-indanone precursors are prepared using the procedure of Taylor et al., supra, from 1,2-bis(bromomethyl)-5-chlorobenzene, 1,2-bis(bromomethyl)-6-chlorobenzene, 1,2-bis(bromomethyl)-4-trifluoromethylbenzene, 1,2-bis(bromomethyl)-4-bromobenzene, 1,2-bis(bromomethyl)-4-fluorobenzene, 1,2-bis(bromomethyl)-3-fluorobenzene, 1,2-bis(bromomethyl)-3,4-dichlorobenzene, 1,2-bis(bromomethyl)-3,4,5,6-tetrachlorobenzene and 1,2-bis(bromomethyl)-3,6-dibromo-4,5-dichlorobenzene, respectively.

A group of 10 each of 0–24 hour II instar *Heliothis virescens* larvae is treated with 1 μl of test compound m-phenoxybenzyl 2-(2-indenyl)-3-methylbutanoate in acetone at three different concentrations by application to the dorsum of the thorax. A group of 10 larvae is treated identically with 1 μl acetone as a control. Larvae are held individually in 30 ml plastic cups provided with artificial medium for 72 hours at 25° and 16 hr photoperiod. After 72 hr, the number of dead is calculated as a percentage of the total number originally treated and then corrected for any mortality in the control groups using Abbott's formula. The $LC_{50}$ of the test compound was less than 0.5%.

What is claimed is:

1. A compound of the formula:

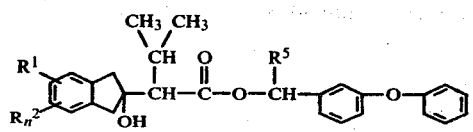

wherein,
n is zero, one, two or three;
each of $R^1$ and $R^2$ is independently selected from hydrogen, chloro, fluoro, bromo, lower alkyl, lower alkoxy and lower haloalkyl; and
$R^5$ is hydrogen, cyano, methyl or ethynyl.

2. A compound according to claim 1 wherein $R^5$ is hydrogen.

3. A compound according to claim 2 wherein each of $R^1$ and $R^2$ is independently selected from hydrogen, chloro, fluoro, bromo, methyl, methoxy and trifluoromethyl.

4. A compound according to claim 2 wherein each of $R^1$ and $R^2$ is independently selected from hydrogen, chloro, fluoro and bromo.

5. A compound according to claim 4 wherein n is one.

6. A compound according to claim 4 wherein n is two.

7. A compound according to claim 4 wherein n is three.

8. A compound according to claim 3 wherein n is zero.

9. A compound according to claim 4 wherein n is zero.

10. A compound according to claim 4 wherein $R^1$ is fluoro and n is zero.

11. A compound according to claim 4 wherein $R^1$ is chloro and n is zero.